(12) United States Patent
Galkin

(10) Patent No.: US 6,975,701 B2
(45) Date of Patent: Dec. 13, 2005

(54) DEVICES FOR PATIENT COMFORT IN MAMMOGRAPHY AND METHODS OF USE

(76) Inventor: Benjamin M. Galkin, 35 Ivy La., Cherry Hill, NJ (US) 08002

(*) Notice: Subject to any disclaimer, the term of this patent is extended or adjusted under 35 U.S.C. 154(b) by 64 days.

(21) Appl. No.: 10/748,891

(22) Filed: Dec. 30, 2003

(65) Prior Publication Data

US 2004/0156472 A1 Aug. 12, 2004

Related U.S. Application Data

(63) Continuation-in-part of application No. 10/302,096, filed on Nov. 22, 2002, now Pat. No. 6,850,590.

(60) Provisional application No. 60/331,993, filed on Nov. 23, 2001.

(51) Int. Cl.$^7$ ................................................. A61B 6/04
(52) U.S. Cl. ......................................... 378/37; 378/165
(58) Field of Search ............................... 378/162–166, 378/37

(56) References Cited

U.S. PATENT DOCUMENTS

| | | | | |
|---|---|---|---|---|
| 4,529,635 | A | * | 7/1985 | Sheldon ..................... 428/40.1 |
| 4,764,948 | A | * | 8/1988 | Hurwitz ....................... 378/165 |
| 5,063,583 | A | | 11/1991 | Galkin ......................... 378/207 |
| 5,276,726 | A | | 1/1994 | Galkin ......................... 378/207 |
| 5,311,883 | A | | 5/1994 | Sherman ..................... 128/846 |
| 5,377,254 | A | | 12/1994 | Walling ....................... 378/167 |
| 5,394,456 | A | | 2/1995 | Livingston .................. 378/162 |
| 5,406,612 | A | | 4/1995 | Galkin ......................... 378/207 |
| 5,412,706 | A | * | 5/1995 | Deibel ......................... 378/162 |
| 5,479,927 | A | | 1/1996 | Shmulewitz ........... 128/660.09 |
| 5,541,972 | A | | 7/1996 | Anthony ....................... 378/37 |
| 5,544,238 | A | | 8/1996 | Galkin ......................... 378/207 |
| 5,706,327 | A | | 1/1998 | Adamkowski et al. ........ 378/37 |

| | | | |
|---|---|---|---|
| 6,049,583 | A | 4/2000 | Galkin ........................ 378/37 |
| 6,333,970 | B1 * | 12/2001 | LeMaitre et al. ........... 378/162 |
| 6,577,702 | B1 | 6/2003 | Lebovic et al. ............... 378/37 |
| 6,765,984 | B2 * | 7/2004 | Higgins et al. ............... 378/37 |
| 2003/0007597 | A1 | 1/2003 | Higgins et al. ............... 378/37 |

(Continued)

FOREIGN PATENT DOCUMENTS

DE                23 35 576              1/1975

(Continued)

OTHER PUBLICATIONS

Galkin, B.M., et al., "The Breast Pillow™: A mammography device for reducing patient discomfort and pain," 2001, 0768BR-e, 1 page.

(Continued)

*Primary Examiner*—Craig E. Church
*Assistant Examiner*—Jurie Yun
(74) *Attorney, Agent, or Firm*—Woodcock Washburn LLP

(57) ABSTRACT

Devices for use with a mammography unit and for patient comfort comprise an x-ray transparent compressible material and a radiopaque identifier which imparts information onto a mammogram about physical and other characteristics of the material that affect image quality. The identifier is generally affixed to the material, and, for example, it can be sealed within the material. The material substantially conforms to patient contact surfaces of a cassette holder (bucky) or a compression paddle and, in one example, contains openings to accommodate passage of a cassette therethrough. The devices are for single use or reusable. X-ray transparent disposable covers used over the devices can also have a radiopaque identifier keyed to desired information about, for example, physical and other characteristics of the material that affect image quality. All information appears away from the breast image.

29 Claims, 6 Drawing Sheets

U.S. PATENT DOCUMENTS

| | | | |
|---|---|---|---|
| 2003/0058987 A1 | 3/2003 | Rick et al. | 378/37 |
| 2003/0174807 A1 | 9/2003 | Lebovic et al. | 378/37 |
| 2003/0194052 A1 | 10/2003 | Price et al. | 378/45 |
| 2004/0081284 A1 | 4/2004 | Livingston | 378/162 |

FOREIGN PATENT DOCUMENTS

| | | |
|---|---|---|
| FR | 2 702 059 | 9/1994 |

OTHER PUBLICATIONS

Galkin, B.M., et al., "The Breast Pillow™: A mammography device for reducing patient discomfort and pain," *Education exhibit presented at the annual meeting of the Radiological Society of North America,* Nov.25-30, 2001, Abstract 0768BR-e published in Supplement to Radiology, 2001, 221(P), p. 698.

Galkin, B., et al., "The Breast Pillow™: A novel device to reduce patient discomfort and pain during mammography while also measuring compression force(1)," *Med. Physics,* Aug. 2001, 28(8), SU-HH-EXH C-10, 1 page.

Galkin, B.M., et al., "The Breast Pillow™: A novel device to reduce patient discomfort and pain during mammography while also measuring compression force," *Poster exhibit presented at the annual meeting of the American Association of Physicists in Medicine,* Jul. 22-26, 2001, Abstract SU-HH-EXH C-10 published in *Med. Phys.,* 2001, p. 1820.

U.S. Appl. No. 60/187,198, filed Mar. 6, 2000, Lebovic et al.

Berns, E. et al., "Effect of Foam Pads on Mammography Dose Calculation", *Medical Physics, 45th Annual Meeting American Association of Physicists in Medicine,* Aug. 10-14, 2003, 2 pages.

* cited by examiner

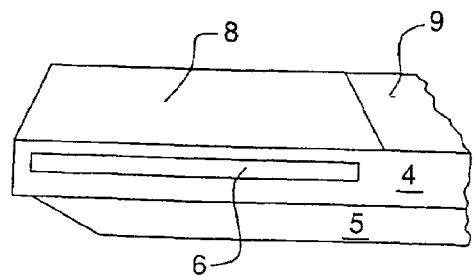
FIG. 3
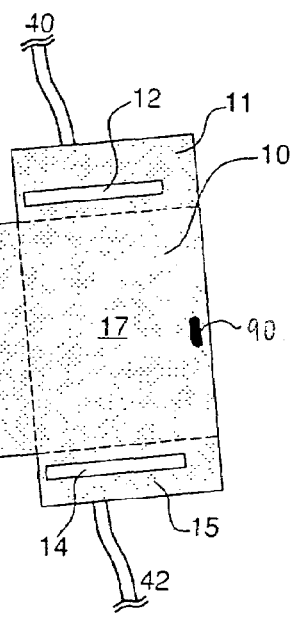
FIG. 4C
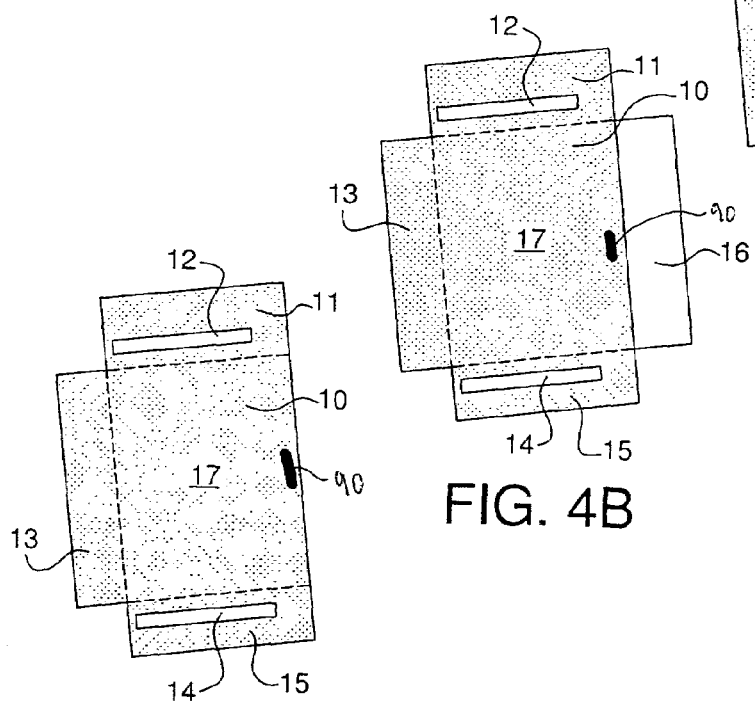
FIG. 4B
FIG. 4A

DEVICES FOR PATIENT COMFORT IN MAMMOGRAPHY AND METHODS OF USE

CROSS-REFERENCE TO RELATED APPLICATIONS

This is a continuation in-part of U.S. application Ser. No. 10/302,096, filed Nov. 22, 2002, now U.S. Pat. No. 6,850, 590, which claims the benefit of priority under 35 U.S.C. § 119(e) from provisional U.S. Application Ser. No. 60/331, 993, filed on Nov. 23, 2001, both of which are incorporated herein by reference in their entirety.

FIELD OF THE INVENTION

The present invention relates to the field of radiology and particularly to mammography. More specifically, the present invention relates to devices and methods for reducing patient discomfort and pain during mammography while providing visible markings on the mammogram that relate to physical properties and other information about comfort devices.

BACKGROUND OF THE INVENTION

Mammography is the process of obtaining x-ray images of the human breast for diagnosis or surgery. It involves positioning a patient's breast in a desired orientation against a cassette holder (also known as a "bucky") of a mammography unit, compressing the breast with a compression device (e.g., a compression paddle), and then exposing the breast to x-rays to create a latent image of the breast on an image receptor. After exposure, the compression device is released. The image receptor is usually a film in contact with an intensifying screen contained within a cassette. The cassette is inserted into a cassette holder before every image is taken and removed after every image. The film is removed from the cassette and developed to produce a radiographic image of the breast.

A complete mammographic study usually involves at least two x-ray exposures of each breast. One exposure is a craniocaudal view in which the breast is compressed in a superior-inferior direction, i.e., from the direction of the patient's head downward, against a tube-side surface of the cassette holder. The plane of the tube-side surface of the cassette holder is parallel to the floor and the x-ray beam is directed vertically downward. A second exposure is a lateral or oblique view in which the breast is compressed mediolaterally, i.e., from the direction of the patient's midline sidewise, against the tube-side surface of the cassette holder which is angled, along with the axis of the x-ray beam, relative to the floor.

The compression device includes a rectangular flat plate, called a compression paddle or a compression plate, which is attached to the mammography unit between an x-ray tube assembly and the cassette holder (also known as a "bucky"). The edges of the paddle or plate are turned upward away from the cassette holder to provide a smooth curved surface for patient comfort. The compression paddle is usually made of thin, light-transparent, plastic that absorbs only a small fraction of the incident x-ray beam. The compression paddle is moved either manually or by power drive to apply a compression force to the breast, thereby flattening the breast against the cassette holder to a near uniform thickness. U.S. Pat. No. 6,049,583 issued to the present inventor discusses methods and apparatus for measuring compression force in mammography. During compressing and imaging, parts of the patient's body come into contact with the compression paddle. After x-ray exposure, the compression force is released for patient comfort.

To properly position the patient's breast in a desired orientation, a technologist is guided by a light beam originating from the x-ray tube assembly that passes through a collimator and the compression paddle and illuminates the area of the cassette holder that will be exposed to x-rays, i.e., the imaging area. As is well known in the field, to properly position the breast, the patient's chest wall or other regions of the body, depending on the desired view, are brought into tight contact with the rigid surfaces of the cassette holder, its edges, and corners. This procedure has the effect of forcing the patent's anatomy to contour to the shape of the cassette holder, which often causes patient discomfort and pain.

Oftentimes, overlapping internal structures are present within the breast tissue that can obscure their delineation in a radiographic image. As a result, it is often necessary to reposition the breast slightly in order to arrive at a diagnosis. This requires repositioning the patient for each view with the attendant discomfort.

During positioning, compressing, and imaging, parts of the patient's body come into contact with the cassette holder. The cassette holder is a rectangular, box-like device that has a flat tube-side surface against which the breast is compressed, a flat outer surface along one edge of the tube-side surface which contacts the patient's chest wall or torso, and two flat side surfaces opposite each other along the other edges that can come into contact with other parts of the patient's anatomy such as the underarm and axilla. Each of the side surfaces has an opening, typically rectangular, to a cassette tunnel. The openings are used for insertion and removal of the cassette. The tube-side surface includes an imaging area, which is transparent to x-rays, located directly above the cassette as it resides in the cassette holder, and where the breast is positioned during imaging, and a solid section which is not transparent to x-rays. Within the cassette holder is an antiscatter grid assembly. The cassette holder is held in position on the x-ray unit by slidably engaging to a support member. Because the surfaces of the cassette holder may come into contact with blood or other infectious material, they must be able to withstand contact with the chemical agents usually used for disinfecting purposes. Cassette holders come in different sizes depending on the size film to be used.

It is well known that many women find the procedure for obtaining a mammogram to be uncomfortable and for some, even painful. Methods to provide patient comfort during the examination involve adding cushioning material to the surfaces of the cassette holder and/or the compression paddle. Some cushioning devices and methods are described in the art as follows.

In U.S. Pat. No. 5,541,972 by Anthony, disposable sanitary cushioning strips that are attached to the outside of the cassette holder are described. The strips are intended to be replaced between patients. The strips are placed to provide cushioning only along the outer surface of the cassette holder, and its edges and corners, where the patient's torso contacts the cassette holder. The Anthony invention, therefore, provides only limited relief for the patient since it does not cushion the breast from contact with the tube-side surface of the cassette holder.

Others in the art use a radiolucent pad, the MammoPad® supplied by BioLucent, Inc. (Aliso Viejo, Calif.), that is placed on the tube-side surface of the cassette holder and is folded over to the outer surface of the cassette holder facing the patient's torso. The pad is held in position by a peel-off layer of adhesive that covers the underside. This device, however, does not cushion the underarm or axilla areas for mediolateral or lateral views unless it is removed and repositioned. Moreover, if it is repositioned for these views, it blocks access to an opening to the cassette tunnel. In addition, a new pad is used for each patient, and many mammography facilities find the cost per pad to be prohibitive under current third party reimbursement schedules. U.S. Pat. No. 6,577,702 issued to Lebovic et al.; U.S. Patent Application Publication Nos. US 2003/0007597 by Higgins, et al. and 2003/0174807 by Lebovic et al. also describe cushioning products.

In U.S. Pat. No. 5,311,883 to Sherman, a sanitary shield for dedicated mammography apparatus is discussed. According to Sherman, the shields are made using known vacuum molding techniques. Therefore, although the shields may be flexible to a certain extent, they are not compressible and would not provide cushioning or reduction of discomfort to a patient.

In U.S. Pat. No. 5,479,927 to Shmulewitz, a gel pad that can be used in conjunction with conventional mammography equipment is discussed. The gel pad is located on the underside of a compression plate and fails to cushion the breast from either the tube-side surface or the outer surface of the cassette holder.

Another product is the Squeeze Ease by S&S X-ray Products (Houston, Tex.). It is described as having an outer thin plastic shell, and an inner foam core.

Comfort devices for patient comfort in mammography is also described in Patent Application Publication No. 2003/0099325 by the present inventor.

It is well known to those in the art that image quality of a mammogram is highly dependent on beam quality, which is a function of several factors including the kilovoltage (kVp) impressed across the anode and cathode of the x-ray tube, the material of the x-ray target (e.g., molybdenum), the inherent filtration of the tube (e.g., beryllium), and the material and thickness of added filtration (e.g., molybdenum). Beam quality is measured in terms of half value layer in aluminum (HVL). Adding material in the path of the x-ray beam has a similar effect to adding filtration, for example, HVL increases. Most modern mammography units automatically adjust x-ray exposure factors, including kVp, according to HVL. Increasing kVp decreases image contrast, and thus reduces image quality.

The degree to which HVL is increased by the addition of a material in the path of the x-ray beam depends on its linear attenuation coefficient, "$\mu$," and thickness, "t,". Linear attenuation coefficient is related to physical density. For example, material described as being made of foam can have a density that varies over a wide range. For example, polyurethane foam can have densities of between about 1.8 and about 2.6 pounds per cubic foot.

Moreover, foam cushioning comes in various thicknesses. The firmness of foam is measured in units of Indentation Force Deflection (IDF) which is determined by indenting (compressing) a foam product 25% of its original height. The amount of force, measured in pounds, required to compress the foam is its 25% measurement. The IDF of cushioning foam can range from between about 21 and about 45 pounds.

With respect to the thickness of the foam, it is known in the art that the sharpness of a radiographic image depends on the object to film distance. The shorter the distance the sharper the image. This is an important consideration when attempting to identify images of breast calcifications which are probably the most important diagnostic indicator of early breast cancer. Interposing cushioning material between the breast and the surface of the cassette holder increases the distance between the calcifications and the film and decreases the sharpness of their images.

Since different kinds of foam can be supplied with varying thicknesses and firmnesses, the application of equal compression force to different cushioning materials can drastically impact arriving at a proper diagnosis. Without intending to be bound by theory, this is likely caused by different distances between the calcifications and the film depending on the cushioning material used which result in different degrees of image sharpness. Knowing exactly what outside factors have impacted a mammogram can be an important consideration in arriving at a correct diagnosis.

Subject to a woman's family health history, women are encouraged to obtain their first mammogram at around age 40 and annually thereafter. In reading and analyzing mammograms, images of a current examination are compared with previous examinations. A radiologist or other medical professional looks for the appearance of and/or changes in diagnostic markers such as micro-calcifications and other internal structures. The difficulty in reading mammograms is that changes in these images can be very subtle and depend in large measure on image quality.

Since a wide variety of cushioning materials may be used in mammography, including some that can have a negative effect on image quality, there is a need for a viewer, e.g., a technologist or a radiologist or other medical professional, be able to determine from the mammogram, for example, that cushioning material was used and the type of cushioning. There is also a need that the mammogram contain a permanent record regarding the nature of the cushion material used.

Further, there remains a great need for comfort devices for use during mammography which can minimize or eliminate the pain and discomfort experienced by the patient. To be useful in clinical practice such devices must also not add significantly to the cost of the examination. There remains a great need to provide an indication on a mammogram to alert the viewer that the quality of the breast image may have been compromised by the use of a comfort device. There also exists a need to provides information to a medical professional, e.g. a technologist or radiologist, regarding the use of comfort devices without compromising the cushioning effect of the materials.

SUMMARY OF THE INVENTION

Mammography comfort devices and methods for reducing patient discomfort and pain during mammography are provided by the present invention. Such devices cushion the patient against contact with the surfaces of the cassette holder that cause patient discomfort and pain. In one embodiment, a cassette holder is constructed with a compressible material, preferably a compressible matrix material, that is integral with surfaces of the cassette holder that contact a patient. The compressible material is preferably x-ray transparent. In a preferred embodiment, the compressible material is a low Z elastic compressible material.

The compressible material optionally comprises at least one chamber for entrapping air. It is understood that air can be permanently trapped in the chamber or forced in and released as needed. In one example, a gas inlet manifold provides pressurized gas, i.e. air, to the compressible material for inflation and a gas outlet manifold provides a route for venting the pressurized gas. The thickness of the chamber when filled with air is, for example, between at least approximately 5 millimeters and approximately 20 millimeters. Upon compression, a portion of a chamber that was approximately 5 millimeters when filled with air, for example, would have a thickness of approximately 1 millimeter. When the compressible material is non-porous, it is suitable to withstand disinfecting chemicals. The compressible material may comprise a plurality of chambers which entrap a gas permanently or have the ability to retain and release the gas.

Cassette holders in accordance with the present invention, in one example, comprise an imaging area which is made with a first compressible material which is transparent to x-rays over the mammography useful kVp range. The remaining patient-contact surfaces, which may include an outer surface, a first side surface, and a second side surface, are made with a second compressible material which is not necessarily transparent to x-rays. Cassette tunnel openings of cassette holders in accordance with the present invention are provided to ensure insertion and removal of mammography cassettes are not impeded.

In another embodiment, a comfort device, used in conjunction with a cassette holder, comprises a compressible material configured to define a cavity for containing the cassette holder which conforms to patient-contact surfaces of a cassette holder. Comfort devices are fabricated with compressible material which is transparent to x-rays over the mammography useful kVp range. One embodiment of the invention comprises a low Z elastic compressible matrix material contoured to stretch over the cassette holder's tube-side surface, outer surface, and side surfaces, edges and corners defined thereby. The sections that cover the side surfaces are configured so that they do not block the cassette tunnel. In a preferred embodiment, all of the surfaces that can come into contact with the patient are non-porous. The compressible material is transparent to x-rays over the mammography useful kVp range. The compressible material, preferably a matrix material, optionally comprises at least one chamber for entrapping air. It is understood that air can be permanently trapped in the chamber or forced in and released as needed. The thickness of the chamber when filled with air is, for example, between at least approximately 5 millimeters and approximately 20 millimeters. Upon compression, a portion of a chamber that was approximately 5 millimeters when filled with air, for example, would have a thickness of approximately 1 millimeter. When the compressible material is non-porous, it is suitable to withstand disinfecting chemicals. The compressible material may comprise a plurality of chambers which entrap a gas permanently or have the ability to retain and release the gas.

Methods for reducing patient discomfort during mammography comprise securing a cassette holder to a mammography unit where the cassette holder comprises patient-contact surfaces and a compressible material integral to the patient-contact surfaces. The compressible material is transparent to x-rays. A patient's breast is then positioned on a tube-side surface of the cassette holder and compression of the breast against the tube-side surface occurs.

Methods for reducing patient discomfort in accordance with another aspect of the present invention include securing a comfort device over a cassette holder to a mammography unit, positioning a patient such that the comfort device is disposed between the patient and patient-contact surfaces, and administering a mammogram.

In a further aspect of the present invention methods for shaping a patient's breast during a mammogram without repositioning comprise securing a cassette holder to a mammography unit wherein the comfort device comprises an inflatable chamber; an inlet manifold operatively associated with the gas source for receiving the gas and supplying the gas to the cassette holder; and an outlet manifold operatively associated with the cassette holder for receiving the gas from the cassette holder; introducing a gas into the inflatable chamber; positioning the breast on the inflatable chamber; compressing the breast forming a first shape; and imaging the first shape of the breast. Further, a portion of the gas can be released to result in the breast forming a second shape; and then the second shape of the breast can be imaged. Optionally, additional gas can be introduced to result in the breast forming a second shape and then the second shape can be imaged. Comfort devices comprising an inflatable chamber; an inlet manifold operatively associated with the gas source for receiving the gas and supplying the gas to the comfort device; and an outlet manifold operatively associated with the comfort device for receiving the gas from the cassette holder are also suitable for methods of shaping a patient's breast without repositioning.

Other embodiments of the present invention comprise comfort devices which comprise an x-ray transparent compressible material adapted with a partially radiopaque identifier, wherein a portion of the identifier comprises indicia which impart information about the material onto a mammogram. For example, it may be desirable to provide information including, but not limited to, the physical properties of a comfort device, such as density or thickness, the location of the device, the manufacturer of the device, and/or the date of manufacture. In accordance with the present invention, information can be provided on the mammogram in an area away from an image of the breast. For example, information about a comfort device that is located on a cassette holder (a bucky) can be positioned in one area of the mammogram and information about a comfort device that is located on a compression paddle can be positioned in another area of the mammogram. Comfort devices containing identifiers used for cassette holders may further comprise cassette holder openings to permit unimpeded placement of a film cassette within the cassette holder.

Compressible material used in accordance with the present invention may be constructed of varying materials that overlay the imaging portion of the cassette holder (or bucky) and/or the compression paddle. For example, it may be desirable to use materials of differing total linear attenuation values to obtain different optical densities on a mammogram. It also may be desirable to use multiple layers of compressible material.

Also in accordance with the present invention, x-ray transparent compressible material can be used in conjunction with an identifying x-ray transparent cover which comprises a partially radiopaque identifier which imparts information onto a mammogram. The identifying cover can be disposable. Furthermore, both the material and the identifying cover can be adapted with an opening or multiple openings to permit a mammography cassette to pass through.

An identifier as used by the present invention is partially radiopaque such that identifying indicia can be either x-ray transparent or radiopaque, and the remaining portion of the identifier would be radiopaque or x-ray transparent, respectively. By reference to the radiopaque nature of an identifier, it is understood that the identifier may not be completely radiopaque, but its radiopacity would be sufficiently different from the radiopacity of the surrounding materials, e.g., x-ray transparent compressible materials or x-ray transparent covers, so as to be recordable, e.g. radiographically, on a mammogram. The identifier can comprise a variety of radiopaque materials, e.g., paper, plastic, or metal. In such an embodiment identifying indicia would be x-ray transparent. If desired, in another embodiment, identifying indicia can be imprinted with radiopaque ink onto x-ray transparent compressible material or x-ray transparent covers.

A mammography unit in accordance with the present invention comprises a compression paddle, a cassette holder, and a comfort device comprising an x-ray transparent material adapted with a partially radiopaque identifier, wherein a portion of the identifier comprises indicia which impart information about the material onto a mammogram.

Methods in accordance with the present invention include reducing patient discomfort during a mammogram and imparting information onto a mammogram about a comfort device, by securing a comfort device, which comprises an x-ray transparent compressible material and a partially radiopaque identifier comprising indicia, to a mammography unit comprising patient-contact surfaces; positioning a patient such that the comfort device is disposed between the patient and the patient-contact surfaces; administering a mammogram; and recording the indicia onto the mammogram. The comfort device can be secured to the cassette holder, the compression paddle, or both. Recording the indicia onto the mammogram can be done, for example, radiographically or electronically or manually.

Other methods for reducing patient discomfort during a mammogram and for imparting information onto a mammogram about a comfort device can comprise securing the comfort device, wherein the comfort device comprises an x-ray transparent compressible material and an identifying cover, comprising x-ray transparent material and a partially radiopaque identifier comprising indicia, to a mammography unit comprising patient-contact surfaces; securing the identifying cover to the mammography unit; positioning a patient such that the comfort device is disposed between the patient and the patient-contact surfaces; administering a mammogram; and recording the indicia onto the mammogram. In some instances, it may be desirable to place the identifying cover below the x-ray transparent compressible material. Alternatively, it may be desirable to place the identifying cover over the x-ray transparent compressible material. Recording the indicia onto the mammogram can be done, for example, radiographically or electronically or manually.

BRIEF DESCRIPTION OF THE DRAWINGS

The present invention will be better understood, and its numerous objects and advantages will become apparent to those skilled in the art by reference to the following detailed description of the invention when taken in conjunction with the following drawings, in which:

FIG. 3 is an enlarged schematic view of a typical cassette holder;

FIG. 4A is a top view of a comfort device in accordance with an embodiment of the invention with optional openings for a cassette holder to pass through, flattened to show sections for covering patient-contact surfaces of a cassette holder; FIG. 4B depicts the comfort device of FIG. 4A comprising an optional section for holding the comfort device in place on the cassette holder in accordance with an embodiment of the present invention; FIG. 4C depicts the comfort device of FIG. 4A comprising optional fasteners for holding the comfort device in place on the cassette holder in accordance with an embodiment of the present invention;

DETAILED DESCRIPTION OF ILLUSTRATIVE EMBODIMENTS

Figure 1:
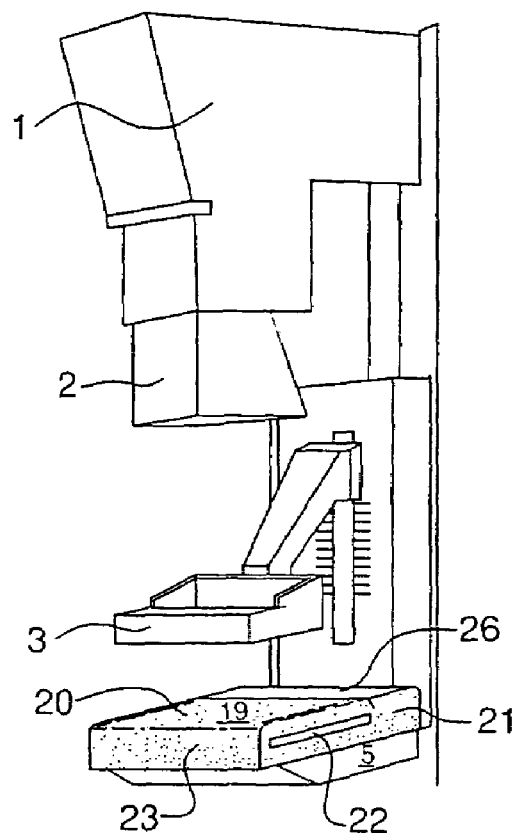
FIG. 1 is a schematic oblique view of a section of a mammography unit illustrating the position of a cassette holder relative to a compression paddle in accordance with an embodiment of the present invention.

This invention describes devices and methods used to minimize and/or eliminate patient discomfort and pain during mammography. Devices and methods that impart onto a mammogram indicia of the presence and physical properties of comfort devices are also provided.

In accordance with the invention, surfaces that contact the patient during mammography comprise compressible material, preferably low Z elastic compressible material. For example, a cassette holder for use with a conventional mammography x-ray unit would comprise compressible surfaces that are integral to the cassette holder. Edges and corners of the cassette holder rounded with a compressible material also to minimize patient discomfort and pain. Cassette holders in accordance with the present invention have at least one compressible surface, preferably a tube-side surface, which changes shape upon compression. Other compressible surfaces may include an outer surface, a first side surface, and a second side surface. Side surfaces are provided with openings for unimpeded placement of cassettes within the cassette holder. Though surfaces are compressible, they do not interfere with insertion and removal of cassettes or the functioning of an antiscatter grid. In one example, the compressible material further comprises non-porous material to provide a surface suitable for disinfecting.

In another example, by reference to an existing cassette holder, a comfort device comprising compressible material which is transparent to x-ray is stretched over the cassette holder to ensure the patient-contact surfaces are cushioned. The patient-contact surfaces include, but are not limited to a tube-side surface, an outer surface, a first side surface, and a second side surface. Upon positioning of the patient's breast on an imaging area of the tube-side surface and subsequent compression, the patient's body is then protected from the rigid surfaces and sharp edges of the bare cassette holder by the presence of the comfort device.

Compressible material may include, but is not limited to, polyethylene materials, polypropylene materials, and rubber foam. Forms of compressible material include, but are not limited to foam, bubble wrap, anti-static, air core, nylon barrier core, tubing, and matrix. For example, low density polyethylene foams provide resiliency and cushioning characteristics suitable to reduce patient discomfort. Bubble wrap, is a further example of material that is compressible and provides cushioning. Furthermore, various forms of high and low density polyethylenes could comprise at least one chamber suitable for inflation. Although rubber foam is compressible, it is preferably suitable for surfaces other than the tube-side due to its potential to interfere with the transmission of x-rays.

Comfort devices in accordance with the present invention are amenable to a wide variety of cassette holder shapes and sizes. Given the adaptability of various compressible materials, comfort devices are constructed to fit around various-sized cassette holders and contain openings to permit insertion and removal of various-sized cassettes. Although allowance is made for the use of conventional x-ray films, it is understood that solid state imaging x-ray systems, which do not comprise cassette tunnels, comprising rigid surfaces and sharp edges and corners that contact the patient would also be amenable to embodiments of the present invention.

Figure 2:
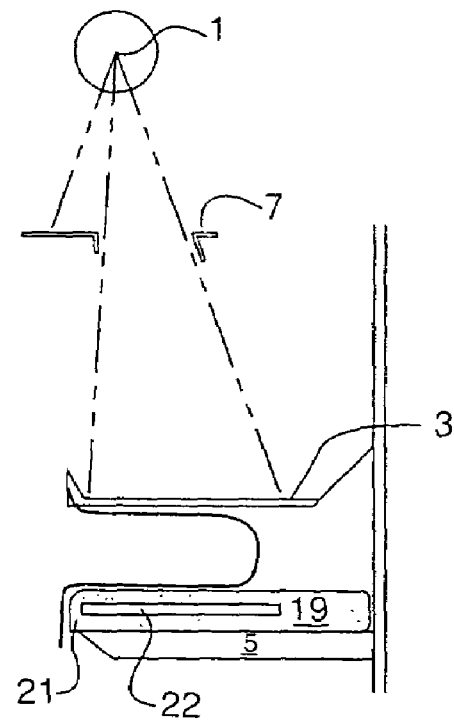
FIG. 2 is a schematic lateral view of FIG. 1 depicting a compressed breast positioned on a cassette holder showing the edge of the cassette holder in contact with the patient's torso.

Referring now to the drawings wherein reference numerals refer to like elements, FIGS. 1 and 2 depict two views of a mammography unit in accordance with an embodiment of the present invention having an x-ray tube 1 that produces x-ray beams (not numbered) connected to a cone 2 that houses a collimator 7. The collimator 7 restricts the size and shape of the x-ray beams in any plane perpendicular to the axis of the x-ray beam. The x-ray beam also passes through a compression paddle 3. Below the compression paddle 3 is a cassette holder 19, which comprises a tube-side surface containing an imaging area 20 and a solid area 26, and a cassette tunnel opening 22. Generally, a cassette tunnel located below the imaging area houses an antiscatter grid and a cassette. The cassette holder 19 is held in place by a support member 5 and slidably engages with a support column (not numbered). X-ray beams pass through imaging area 20 to expose a film in the cassette. The solid area 26 is typically not transparent to x-ray beams and secures the cassette holder to the support column. A patient's breast (not numbered) is positioned on the imaging area 20 of the tube-side surface of the cassette holder 19 and is compressed by the compression paddle 3.

FIG. 3 in an enlarged schematic view of a typical cassette holder 4 positioned on a support member 5, comprising a cassette tunnel 6, an imaging area 8, and a solid area 9.

FIG. 4A is a top view of a comfort device 17 in accordance with the invention with optional openings, flattened, to show sections 10, 11, 13, and 15 for covering patient-contact surfaces of a cassette holder, depicted, for example, in FIG. 3. In one example, a comfort device 17 is fabricated with a compressible material. Compressible material is preferably low Z elastic matrix material that entraps air. The material can comprise a cushion of air which permanently entraps air. The material can also comprise a plurality of cushions. Alternatively, the material can comprise at least one inflatable chamber to contain air that can be forced or pumped into the comfort device. The compressible material comprises a section 10 for covering the imaging area 8. The device also comprises sections 11, 13, and 15 for covering other surfaces of the cassette holder that can come into contact with a patient during mammography. Sections 11 and 15 can have optional openings 12 and 14, typically rectangular, to facilitate the insertion and removal of a cassette in the cassette holder. In one example, adhesive strips are suitable for securing the underside of the comfort device to the cassette holder. An identifier 90 is partially radiopaque such that information about the compressible material can be imparted onto a mammogram.

In another example, as shown in FIG. 4B, the comfort device of FIG. 4A is depicted with optional section 16 which is an extension of the compressible material that can be adapted with methods for retaining the compressible material in place on the cassette holder. Furthermore, there is no limitation on the material used to fabricate section 16. Although compressible material may be used to facilitate ease of manufacture of the comfort device, it is understood that oftentimes section 16 need not be x-ray transparent, because x-ray beams do not need to penetrate that area, nor compressible, because a patient typically does not contact that area. Section 16 can be integral with the comfort device or attached separately.

In yet a further example, as shown in FIG. 4C, the comfort device of FIG. 4A is depicted with optional fasteners 40 and 42 which secure the device by wrapping around the underside of the support member 5. One fastener is shown on each opposite side of the comfort device, however, it is contemplated that multiple fasteners are suitable for attaching along either side. Furthermore, one fastener can be used which secures to an opposite side of the comfort device.

In one example, fasteners can be straps that meet underneath the support member and tie together. In another example, fasteners can engage with each other using hook and loop fasteners. Yet another embodiment includes fasteners that can be one-piece elastic bands which are fixed to opposite sides of the comfort device. The fasteners can be fabricated of any material suitable for fastening and unfastening. For ease of manufacture, however, it may be desirable to fabricate the fasteners out of the compressible material of the comfort device. Fasteners can be integral with the comfort device or attached separately.

Figure 5:
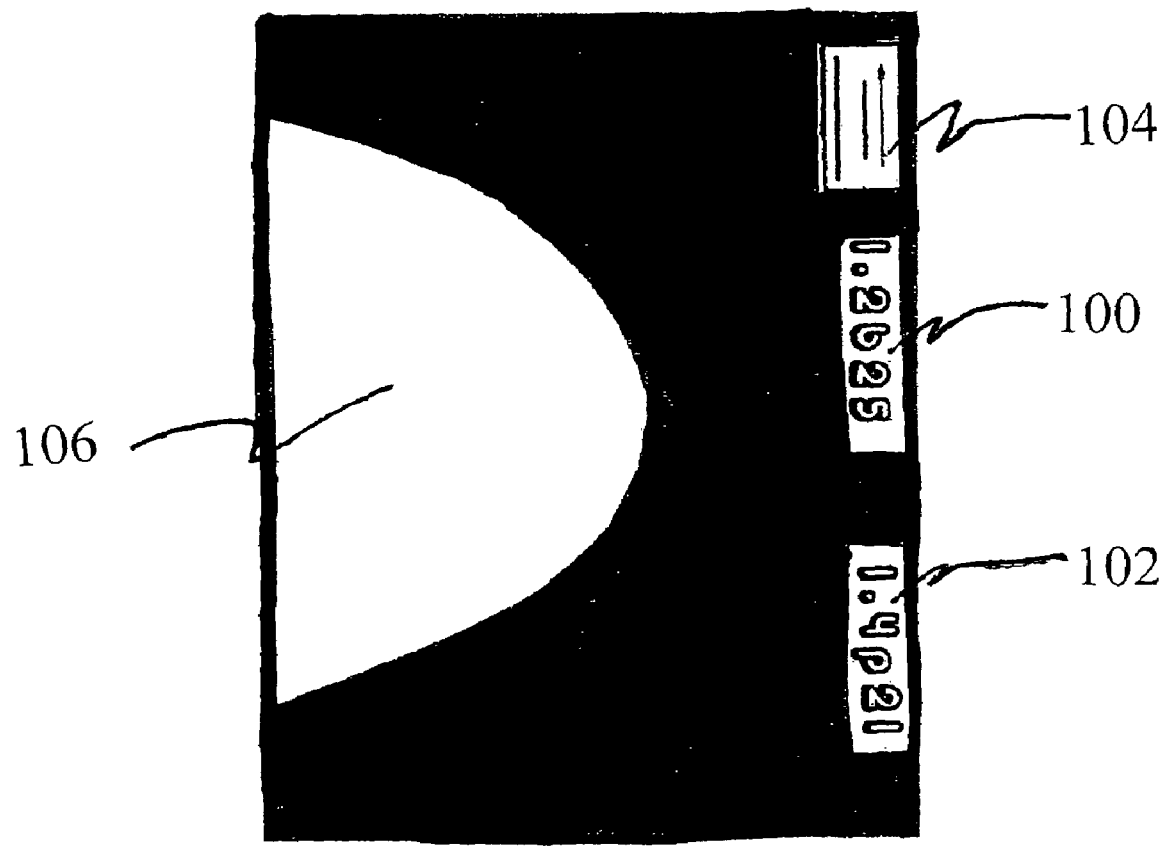
FIG. 5 is a schematic mammogram obtained using the comfort devices comprising partially radiopaque identifiers in accordance with the present invention.

FIG. 5 is a schematic mammogram obtained using comfort devices comprising partially radiopaque identifiers according to the present invention. An image of a breast 106 is shown on the mammogram. Quality control information and patient identifying information 104 can be transferred onto the mammogram electronically by a technologist. In accordance with the present invention, identifying information 100 pertaining to a comfort device used on a tube-side surface and/or patient-contact surfaces of a cassette holder is imparted onto the mammogram by the use of a partially radiopaque identifier. Identifying information pertaining to a comfort device used on patient-contact surfaces of a compression paddle holder 102 is imparted onto the mammogram by the use of a partially radiopaque identifier. Information imparted by indicia is practically unlimited, as it may be desirable to provide information about the device's manufacturer, date of manufacture, physical properties, and/or location. Physical properties may include, but are not limited to, physical density and/or compressibility.

Figure 6:
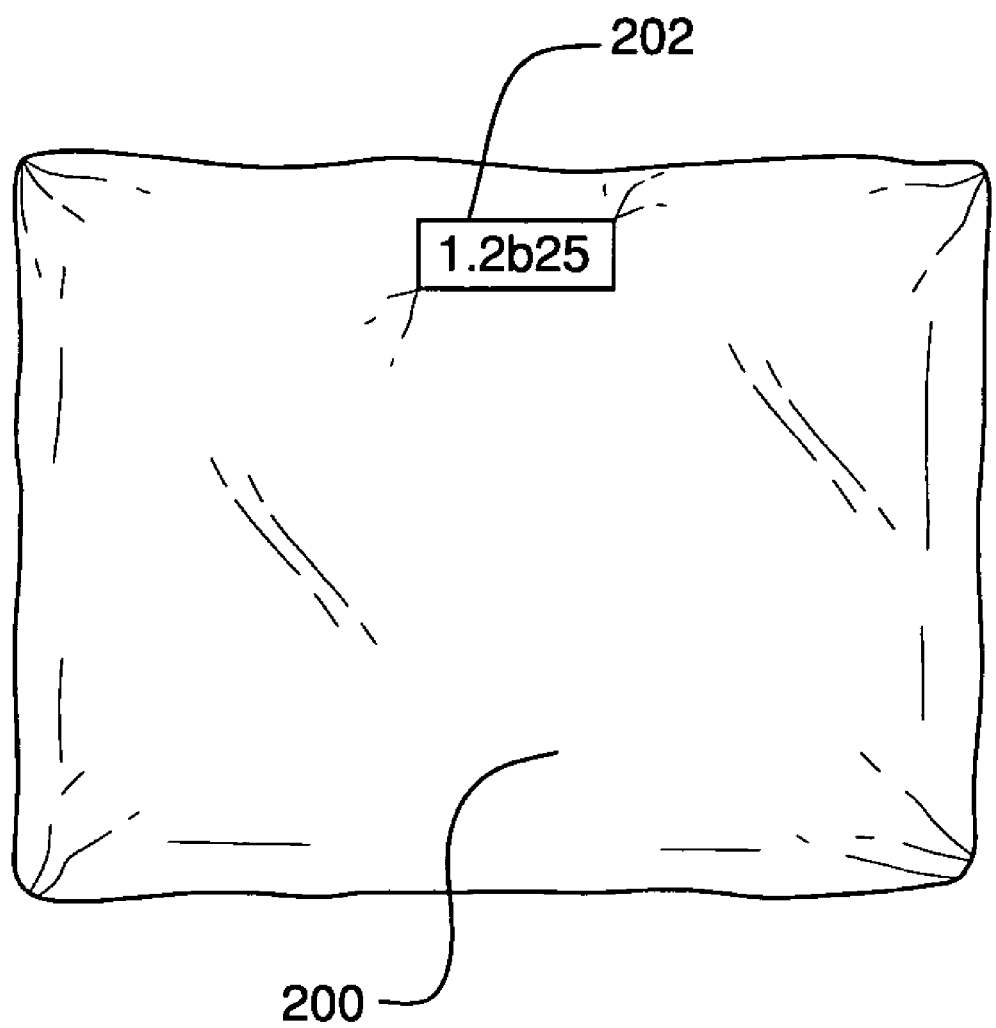
FIG. 6 is an x-ray transparent cover comprising indicia.
Figure 7A:
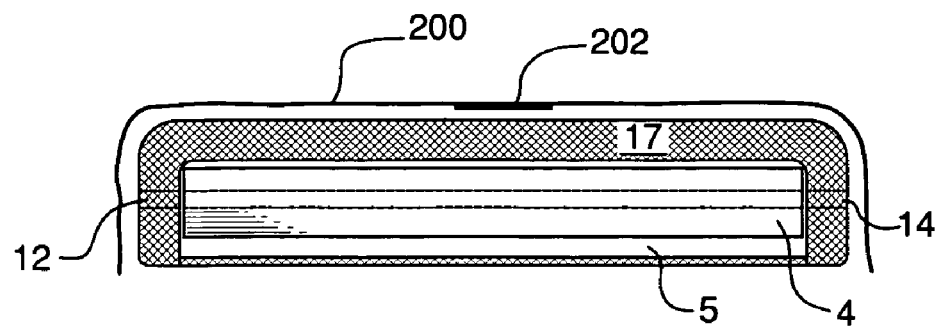
FIG. 7A is an example of an x-ray transparent cover comprising indicia that can be draped over a cushioned cassette holder.
Figure 7B:
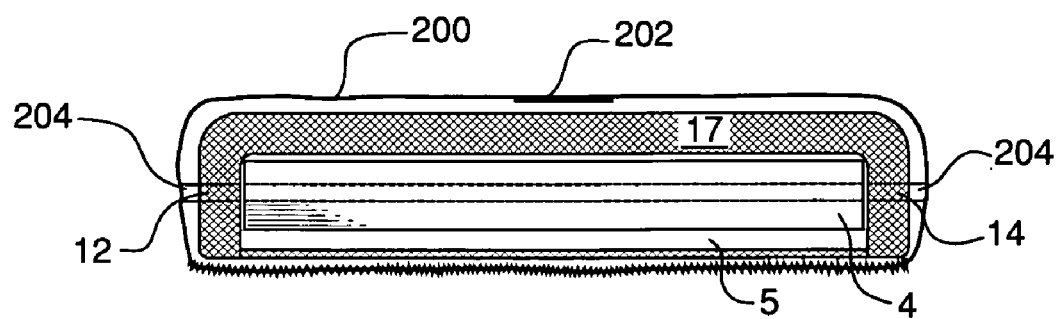
FIG. 7B is an example of an x-ray transparent cover comprising indicia that can be fitted over a cushioned cassette holder and support arm, where the cover has optional side openings.
Figure 8:
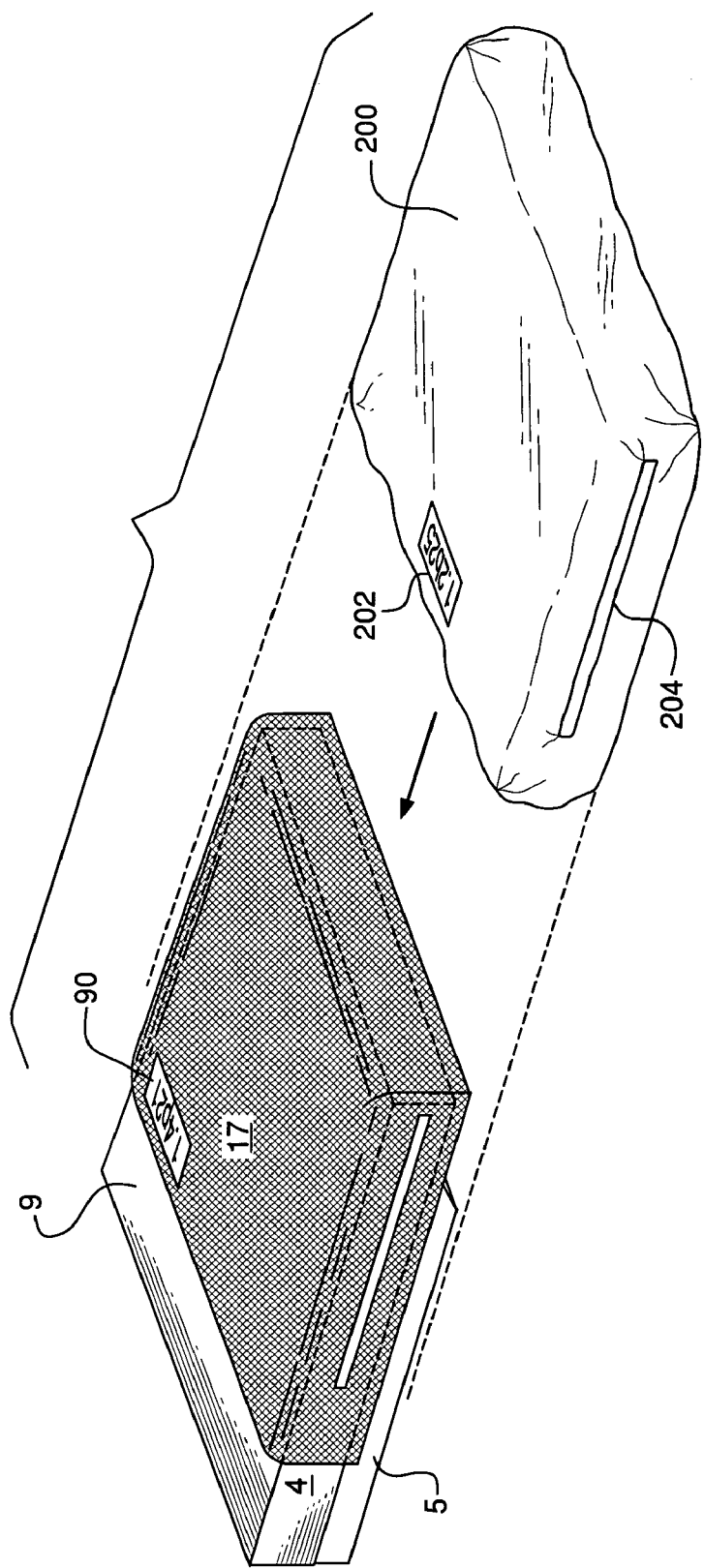
FIG. 8 is an x-ray transparent cover comprising indicia which is offset from a cassette holder which has a compressible x-ray transparent material.

Location of an identifier on a mammogram is preferably outside the area of where the breast is imaged. The partially radiopaque identifier can be located, either permanently or temporarily, for example, on a top surface of an x-ray transparent compressible material, or on a bottom surface, or even within the body of the material. Should more than one layer of compressible material be used, an identifier can be located between the layers. The identifier can also be removably attached to the compressible material, using a radiotranslucent fastener, for example tape. In some instances, it may be desirable to locate the identifier on a surface of the compression paddle or cassette holder or both. As shown in FIG. 6, one or more identifiers 202 can also be located on or within an x-ray transparent cover 200 which in turn can be positioned below or above the compressible material as desired. FIG. 7A depicts one embodiment exemplifying a combination of an x-ray transparent cover 200 comprising indicia 202 which is draped over the compressible material 17 of a cassette holder 4 which is positioned on a support arm 5. Openings 12 and 14 are provided in the compressible material, but due to the draped-nature of the transparent cover 200, corresponding openings in the cover are optional. FIG. 7B shows another embodiment of an x-ray transparent cover 200 comprising indicia 202 which fits around a cassette holder 4 having compressible material 17 wherein the cassette holder 4 is positioned on a support arm 5. The transparent cover 200 optionally comprises at least one opening 204 which is adapted to permit a mammography unit cassette to pass therethrough and can conform to surround the compressible material 17 and support arm 5. FIG. 8 shows an x-ray transparent cover 200 comprising indicia 202 and an optional opening 204. the cover being offset from a cassette holder 4 having compressible material 17. which optionally also has indicia 90. An identifier can simply be a radiopaque material, for example metal (or plastic or paper) which is placed on a comfort device before a mammogram is taken. Indicia which impart information about the comfort device can be x-ray transparent when the rest of the identifier is radiopaque. On the other hand, should the indicia be radiopaque, then the remaining material of the identifier would be radiotranslucent.

Identifiers as discussed in accordance with the present invention can be used along with all types of comfort devices used in conjunction with all types of imaging equipment. Furthermore, comfort devices can be attached to imaging equipment in various ways without impacting the utility of the comfort device adapted with an identifier. It is particularly desirable to use identifiers during mammography where comfort devices are used to alert a radiologist or other medical professional that material was in the path of the x-ray beam which may have impacted the image of the breast. It is understood, however, such an indication may be desirable in other imaging disciplines.

Further, in accordance with the present invention, cassette holders are provided wherein x-ray transparent compressible material adapted with an identifier is integral to the cassette holder. Compression paddles with x-ray transparent compressible material adapted with an identifier integral to the compression paddle are also provided.

While the invention has been described and illustrated with reference to specific embodiments, those skilled in the art will recognize that modifications and variations may be made without departing from the principles of the invention as described herein and set forth in the following claims.

What is claimed:

1. A comfort device for use with a mammography unit comprising:
   an x-ray transparent compressible material and a partially radiopaque identifier that is permanently affixed to said compressible material, wherein a portion of said identifier comprises indicia which impart information about said material onto a mammogram.

2. The comfort device of claim 1 wherein said information is imparted onto said mammogram in an area away from a breast image.

3. The comfort device of claim 1 wherein said information is a symbol or word or bargraph or combinations thereof which indicate physical properties or manufacturer or location or combinations thereof about said comfort device.

4. The comfort device of claim 1 wherein said indicia is imprinted on said comfort device.

5. The comfort device of claim 1 wherein a portion of said identifier is radiopaque, said portion comprising paper or metal or plastic or combinations thereof and said indicia are x-ray transparent.

6. The comfort device of claim 1 wherein said identifier is embedded within said compressible material.

7. The comfort device of claim 1 configured to define a cavity for containing a cassette holder, wherein said material substantially conforms to patient-contact surfaces of said cassette holder and wherein said indicia imparts information onto a first area of said mammogram.

8. The comfort device of claim 7 further comprising a cassette holder opening.

9. The comfort device of claim 1 configured to define a cavity for containing a compression paddle, wherein said material substantially conforms to patient-contact surfaces of said compression paddle and wherein said indicia imparts information onto a second area of said mammogram.

10. The comfort device of claim 1 wherein said x-ray transparent compressible material comprises a first area comprising a first total linear attenuation value and a second area comprising a second total linear attenuation value.

11. A comfort device for use with a mammography unit, comprising an x-ray transparent compressible material, an identifying cover, and a first partially radiopaque identifier permanently affixed to said identifying cover, wherein said identifying cover comprises x-ray transparent material and said first partially radiopaque identifier imparts information about said compressible material onto a mammogram.

12. The comfort device of claim 11 wherein said identifying cover is disposable.

13. The comfort device of claim 11 wherein said compressible material is adapted with a first opening and said cover is adapted with a second opening, both openings adapted to permit a mammography unit cassette to pass therethrough.

14. The comfort device of claim 11 further comprising a second partially radiopaque identifier permanently affixed to said x-ray transparent compressible material, wherein said second partially radiopaque identifier imparts information about said compressible material onto a mammogram.

15. The comfort device of claim 11 wherein said first partially radiopaque identifier is sealed within said identifying cover.

16. A method for reducing patient discomfort during a mammogram and for imparting information onto a mammogram about a comfort device, comprising:
   securing said comfort device, wherein said comfort device comprises an x-ray transparent compressible material and a partially radiopaque identifier comprising indicia that is permanently affixed to said compressible material to a mammography unit comprising patient-contact surfaces;
   positioning a patient such that said comfort device is disposed between said patient and said patient-contact surfaces;
   administering a mammogram; and
   recording said indicia wherein said indicia imparts information about said compressible material onto said mammogram.

17. The method of claim 16 comprising securing said comfort device to a cassette holder.

18. The method of claim 16 comprising securing said comfort device to a compression paddle.

19. The method of claim 16 wherein said indicia are recorded radiographically onto said mammogram.

20. A method for reducing patient discomfort during a mammogram and for imparting information onto a mammogram about a comfort device comprising:
   securing said comfort device, wherein said comfort device comprises an x-ray transparent compressible material, an identifying cover, and a partially radiopaque identifier, wherein said cover comprises x-ray transparent material, wherein said partially radiopaque identifier is permanently affixed to said identifying cover and comprises indicia, to a mammography unit comprising patient-contact surfaces;

securing said identifying cover to said mammography unit;

positioning a patient such that said comfort device is disposed between said patient and said patient-contact surfaces;

administering a mammogram; and recording said indicia wherein said indicia imparts information about said compressible material onto said mammogram.

21. The method of claim 20 further comprising positioning said identifying cover underneath said x-ray transparent compressible material.

22. The method of claim 20 wherein said identifying cover is disposable.

23. The method of claim 22 further comprising positioning said identifying cover over said x-ray transparent compressible material.

24. A mammography unit comprising:
 a compression paddle;
 a cassette holder; and
 a comfort device comprising an x-ray transparent compressible material and a partially radiopaque identifier that is permanently affixed to said compressible material, wherein a portion of said identifier comprises indicia which impart information about said comfort device onto a mammogram.

25. A method for recording the use of a comfort device in conjunction with a mammography unit comprising:
 securing said comfort device comprising an x-ray transparent compressible material and a partially radiopaque identifier that is permanently affixed to said compressible material, said identifier comprising indicia about said material, to a mammography unit;
 exposing said comfort device and said identifier to x-rays; and
 producing a radiographic image of said indicia wherein said indicia comprises information about at least one physical property of said material.

26. The method of claim 25 wherein said information comprises a total linear attenuation value of said material.

27. The method of claim 25 further comprising administering a mammogram, simultaneously exposing a patient's breast and said identifier to x-rays; and producing a radiographic image of said breast and said indicia wherein said indicia comprises information about at least one physical property of said material.

28. A method for recording the use of a comfort device in conjunction with a mammography unit comprising:
 securing said comfort device comprising an x-ray transparent compressible material and a partially radiopaque identifier that is permanently affixed to said compressible material, said identifier comprising indicia about said material, to a mammography unit;
 exposing said comfort device and said identifier to x-rays; and
 producing a radiographic image of said indicia wherein said indicia comprises information about the manufacturer or product name or both of said material.

29. The method of claim 28 further comprising administering a mammogram, simultaneously exposing a patient's breast and said identifier to x-rays; and producing a radiographic image of said breast and said indicia wherein said indicia comprises information about the manufacturer or product name or both of said material.

* * * * *